(12) United States Patent
Goebel Quintana

(10) Patent No.: US 8,814,349 B2
(45) Date of Patent: Aug. 26, 2014

(54) ONE-PIECE LENS WITH SURPLUS INNER OPTICAL MATERIAL

(76) Inventor: Alejandro Arturo Goebel Quintana, Ciudad Satelite (MX)

( * ) Notice: Subject to any disclaimer, the term of this patent is extended or adjusted under 35 U.S.C. 154(b) by 115 days.

(21) Appl. No.: 13/380,155

(22) PCT Filed: Jun. 25, 2010

(86) PCT No.: PCT/MX2010/000057
§ 371 (c)(1),
(2), (4) Date: Feb. 14, 2012

(87) PCT Pub. No.: WO2010/151097
PCT Pub. Date: Dec. 29, 2010

(65) Prior Publication Data
US 2012/0127425 A1    May 24, 2012

(30) Foreign Application Priority Data
Jun. 26, 2009 (MX) .................. MX/u/2009/000230

(51) Int. Cl.
*G02C 7/10* (2006.01)
(52) U.S. Cl.
USPC ............... 351/159.01; 351/44; 351/159.6; 351/159.67; 351/159.75
(58) Field of Classification Search
USPC ............... 351/44, 49, 159.01, 159.75
See application file for complete search history.

(56) References Cited

U.S. PATENT DOCUMENTS

| | | | |
|---|---|---|---|
| 5,137,344 A | 8/1992 | Kagei | |
| 5,550,599 A | 8/1996 | Jannard | |
| 5,689,323 A | 11/1997 | Houston et al. | |
| 5,969,789 A * | 10/1999 | Houston et al. | 351/159.01 |
| 6,382,790 B1 * | 5/2002 | Girod | 351/159.74 |
| 7,011,409 B2 | 3/2006 | Nishikata | |
| 2005/0146677 A1 | 7/2005 | Nishikata | |
| 2008/0051012 A1 * | 2/2008 | Akiyama et al. | 451/42 |
| 2009/0064481 A1 * | 3/2009 | Lemaire et al. | 29/557 |
| 2009/0201463 A1 * | 8/2009 | Carlson | 351/174 |

OTHER PUBLICATIONS

International Search Report in PCT/MX2010/000057, published Dec. 29, 2010.
International Preliminary Report on Patentability with Notification Concerning Transmittal of International Search Report in PCT/MX2010/000057, dated Jan. 12, 2012.

* cited by examiner

*Primary Examiner* — Jordan Schwartz
(74) *Attorney, Agent, or Firm* — Cook Alex Ltd.

(57) ABSTRACT

A one-piece lens is made from optical material and includes an outside part and an inside part, in which the inside parts comprise a surplus amount of the same optical material as the lens, for the purpose of cutting ophthalmic lenses, said surplus material being positioned close to the central part of the lens.

5 Claims, 3 Drawing Sheets

ONE-PIECE LENS WITH SURPLUS INNER OPTICAL MATERIAL

TECHNICAL FIELD

The invention relates to optical devices and especially to an optical quality one-piece lens, with a piece of the same optical material integrated as surplus material on the inside part, for the purpose of cutting the required ophthalmic prescription.

BACKGROUND OF THE INVENTION

Ultraviolet radiation and infrared radiation are invisible to the human eye and it is thus necessary to protect ourselves against them because they are not detected by our eyes. The effects caused by said radiation on the retina are cumulative and thus a continuous exposition to high radiation environments may cause, with the passing of time, irreversible damage to the photosensing elements of the central zone of the retina, causing a process leading to blindness or eye damage. There are natural protection mechanisms, such as pupil contraction and eyelid closure; however, said mechanisms only activate themselves when the visible radiation is intense, but do not detect invisible radiations. It is thus important to use protective lenses for the eyes.

Protective filters incorporated into the lenses of ophthalmic or non ophthalmic sunglasses and clear lens glasses are used to protect our eyes against damaging solar radiations, as well as to reduce eye fatigue and improve visual perception. The use of protective solar lenses or clear lenses, with or without ophthalmic graduation, is everyday more necessary because of the current atmospheric conditions.

Sunglasses and clear filter glasses can be neutral or graduated, and can incorporate the optical correction necessary for correcting the various refractive defects such as: myopia, hypermetropia, astigmatism, presbyopia, phorias, prismated, and same are worn not only as an element protecting against solar radiations but also for aesthetic reasons.

The size and shape of the glasses are especially important under conditions of high solar exposition or damaging radiation, and should not leave areas unprotected. For this reason, wrap around lenses are desirous for glasses to provide lateral protection and good peripheral vision.

The use of neutral or graduated sunglasses and clear filter glasses recently has become more common and necessary. The fast degradation of the ozone layer allows damaging solar radiation passage, leading to an increased use of glasses as dressing accessory. However, for persons wearing prescription lenses, there are few glasses or safety glasses alternatives for solar protection or for sporting activities, and in some cases the wearer has to buy different separate prescription lenses that are adapted to a given type of glasses.

On the other hand, there is a wide range of conventional frames on the market for cosmetic purposes (for solar protection), glasses for motorcyclists, welders, for swimming purposes, etc., including twin rimmed glasses or one-piece lens, that are wide with very high external base curves that functions so a person with eye amitropia could use them as protection or fashion together with their indicated optical correction. Their main function of these types of wrap around lenses is to protect against damaging radiation, against dust or aggressive elements that could impact the eyes and protect against glare with shadows and covers placed on the lens.

In the state of the art there is eyewear that attempts to solve the problem of supplying protection against impacts and integrating the graduation necessary for the wearer. They are described in U.S. Pat. No. 6,502,937 and No. 7,055,951 in which an insert is used for mounting the ophthalmic lenses on the frame.

U.S. Pat. No. 6,502,937 describes eyewear comprising: an eyewear frame, at least one lens in the eyewear frame, and an attachment device for holding prescription lens inserts so that the prescription lens insert is held in a position adjacent the lens of the eyewear thereby correcting the vision of the wearer of the eyewear, further comprising a nose bridge attached to the frame of the eyewear, the attachment device being attached to the nose bridge, and wherein the attachment device comprises a horizontally extending channel in the nose bridge opening rearwardly, and further wherein the prescription lens insert comprises two prescription lens inserts, one for each eye of the wearer connected by a bridge, and wherein the bridge is received in the channel of the nose bridge, and further wherein the bridge is inserted slidably into the rearwardly opening channel.

On the other hand, U.S. Pat. No. 7,055,951 discloses a safety eyewear assembly that includes safety eyewear and a prescription lens insert. The safety eyewear includes a frame having a brow bar configured to extend across the brow of the wearer and further includes a plurality of raised shoulders spaced along the brow bar and an unitary safety lens removably mounted adjacent to the outer surface of the brow bar, wherein vertically extending venting channels are formed between the outer surface of the brow bar and an inner surface of the lens. The prescription lens insert includes a left lens frame configured for receiving a prescription lens, a right lens frame configured for receiving a prescription lens and a connection wire configured to be received in interfitting mating relationship with at least one of the raised shoulders of the brow bar and further configured to extend to the venting channels such that the sculpted wire is releasably captured between the outer surface of the brow bar and the inner surface of the lens.

Moreover, U.S. Pat. No. 6,196,678 and No. 6,604,823 and U.S. Patent Application Publication No. 2003/0142264 disclose a protection lens with ophthalmic graduation necessary for the wearer.

U.S. Pat. No. 6,196,678 discloses a protective eyewear device comprising: a single piece, protective eye shield that includes at least one vision correcting portion, said protective eye shield being adapted to fit a person's head, said single piece, protective eye shield having a left half and a right half, said at least one vision correcting portion being constructed from the same piece of material as said single piece protective eye shield, whereby said at least one vision correcting part is integral with said single piece, protective eye shield, and a right temple and a left temple, said right temple being attached to said right half, said left temple being attached to said left half, said right temple and said left temple each having a protective side shield.

On the other hand, U.S. Pat. No. 6,604,823 describes a magnifying safety glasses assembly for use by persons with presbyopia, the assembly consisting of: a front safety eyepiece portion made substantially of a transparent, non-magnifying, shatter-proof material, and matching right and left temple portions, each affixed to an end of the front eyepiece portion, wherein the front safety eyepiece portion includes at least one built-in magnifying corrective segment for correction of a user's near vision.

Moreover, U.S. Patent Application Publication No. 2003/0142264 discloses safety glasses comprising a one-piece unitary lens having a left eye plano-convex portion and a right eye plano-convex portion, each portion having a radius of curvature ranging for 5 to 8 diopters. An eye corrective lens segment is integrally placed in each the plano-convex portion. The eye corrective segments each are preferably semi-circular with a straight upper edge and surrounded by the plano-convex portion. Side shields are integrally formed with the lens. A frame has a top piece extending across the lens and side shields, and temples are hingedly connected to the top piece.

The pieces of optical material currently used in the optical industry have a circular design and specific diameters that only allow to process ophthalmic prescription lenses in the existing machineries, limiting the assemblies of eyeglasses, solar cosmetic protection, personal protection, or sport lenses on large frames or with high base curves.

SUMMARY OF THE DISCLOSURE

An embodiment supplies a large size one-piece lens with surplus optical material for manufacturing integrated ophthalmic lenses and for solving at the same time the needs of amitropia correction of the wearer, combining protection and fashion in one single product.

A further embodiment supplies a large size one-piece lens with surplus optical material strategically located and of optimum reduced sizes for manufacturing the integrated ophthalmic lenses, generating thus savings in the manufacturing process because this avoids the requirement to abrade the whole inside part of the one-piece lens.

A further embodiment supplies a lens that, because of its curvature and edge thinness, can be adapted to any type of frame, offering thus a lighter and more attractive device.

A further embodiment supplies a lens the function of which is to offer twin lenses with integrated ophthalmic lenses for placement on large frames, with base curves that are usually rejected for ophthalmic mounting or assembly, with clear or sun tinting, or any type of optical finishing or covering applied to the front side or back side, or both.

A further embodiment offers an excellent optical quality because the aesthetic lens and the graduated lens are fused in one single plane.

A further embodiment supplies graduated lenses for someone needing same for conducting their activities, a protection and a fashionable aesthetic element for their eyes in one single lens, wherein the prescription lenses are directly integrated without the need of additional fixtures and/or accessories.

A further embodiment supplies a one-piece lens free from obstruction, obtaining lenses with a wider wrap-around panoramic vision offering comfort to the user.

The above is obtained with an optical material one-piece lens comprising an outside part and an inside part, in which the inside part comprises a surplus amount of the same optical material as the lens, for the purpose of cutting ophthalmic lenses, said surplus material being positioned close to the central part of the lens.

BRIEF DESCRIPTION OF THE DRAWINGS

In order to facilitate the understanding of the invention, hereinafter a description of the instant invention is offered together with the attached drawings wherein.

DETAILED DESCRIPTION OF THE PREFERRED EMBODIMENT

Figure 1:
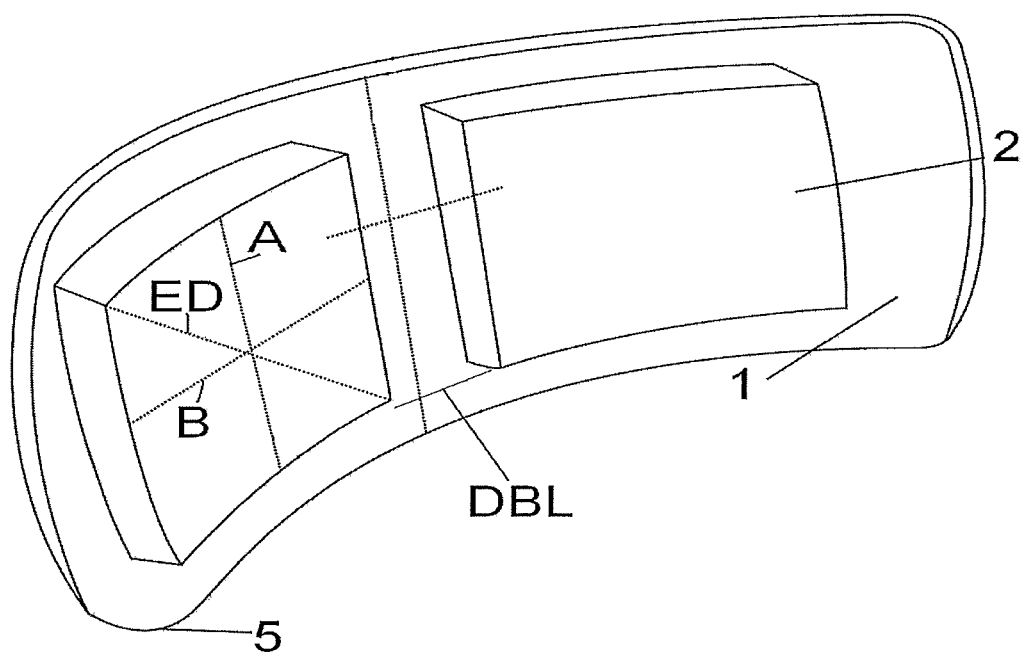
FIG. 1 is a perspective view of the back part of the wrap-around panoramic one-piece lens with an integrated surplus amount of optical material for the making of the integrated ophthalmic lenses of the instant invention.
Figure 2:
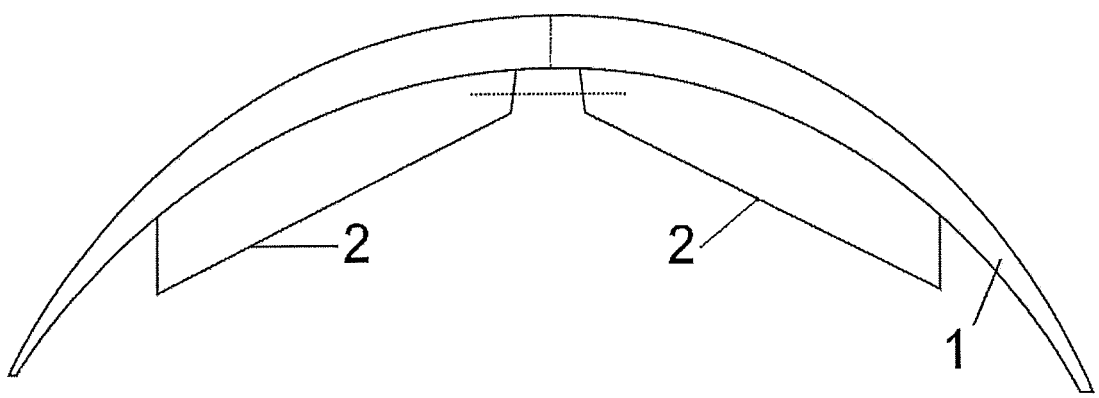
FIG. 2 is a top view of the wrap-around panoramic one-piece lens with integrated surplus amount of optical material for the making of the integrated ophthalmic lenses of the instant invention.
Figure 3:
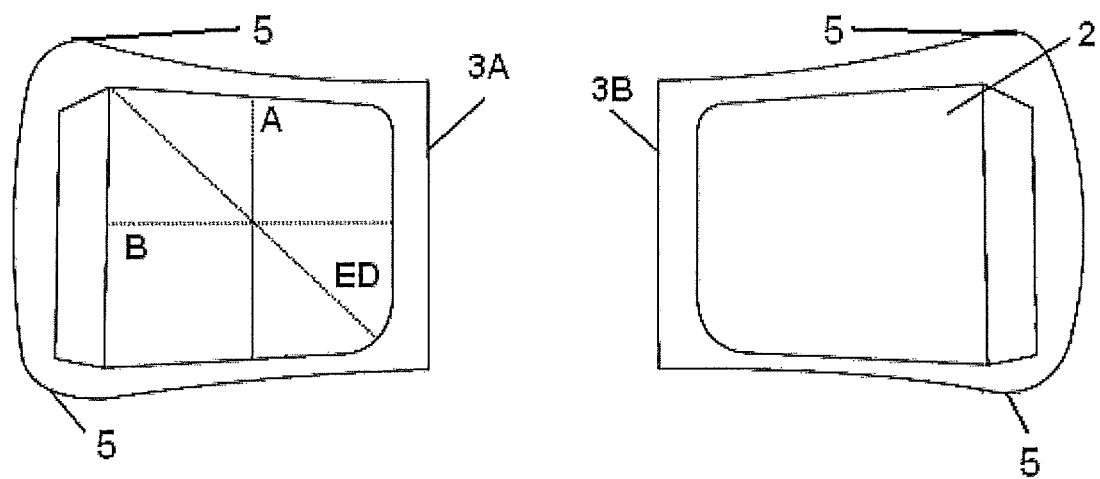
FIG. 3 is a perspective view of the back part of the wrap-around panoramic one-piece lens with an integrated surplus amount of optical material for the making of the integrated ophthalmic lenses of the instant invention, wherein it is shown as they separate in two parts, one right side part and one left side part for mounting on large twin frames.

In FIGS. 1 to 3, a wrap-around panoramic one-piece lens is shown with integrated surplus amount 2 of optical material for the making of the integrated ophthalmic lenses of the instant invention.

The lens 1 comprises an external base curve that can have a torical, bitoric, spherical, bispherical, cylindrical, bicylindrical, aspheric, biaspheric base or combinations thereof for use in neutral non-ophthalmic lenses and in ophthalmic correction prescription lenses.

The wrap-around panoramic one-piece lens 1 can be produced under any known injection or casting method and produced in any number of external and/or internal base and made of any type of optical material indicated for ophthalmic and non-ophthalmic lenses.

The manufacturing material can be transparent, photochromatic, shaded, with mirrored characteristics or of any other embodiment, treatment or covering for ophthalmic and non-ophthalmic lenses placed in the front or back side, or on both sides.

One feature of this embodiment of the invention is to convert lenses with a large frame into lenses with a large frame integrated with optical correction of any type.

The wrap-around panoramic one-piece lens 1 with wide peripheral vision is contemplated exclusively for manufacturing ophthalmic lenses integrated into a one-piece lens.

Ophthalmic lenses are obtained through an integrated piece 2 of internal surplus volume of optical material, of the same material as the material constituting the one-piece lens 1, located in the inside part of the lens 1, for cutting the prismatic, diopter sizes for placing the optical centers and segments of addition of near and intermediate vision requested in the ophthalmic prescription, obtained through any known technique of cutting and generating ophthalmic lenses. Prescription optical lenses of any know type can be manufactured in the piece 2 of internal surplus volume of optical material integrated into the wrap-around panoramic one-piece lens 1 without the need of glue, conventional assembly bevel, interfitting, insert or known assembly adaptations.

The piece 2 of internal surplus volume of optical material, needed for cutting and obtaining the requested ophthalmic prescription integrated to the wrap around panoramic one-piece lens 1 has a material thickness of at least 12 mm measured at the geometrical center with a digital micrometer or Vernier, including in the resulting size the wrap around panoramic one-piece lens 1 that can be formed in accordance with a requested prescription in the material combination.

The pieces 2 can have the shape of irregular polygons with rounded edges and will be positioned towards the nose side (central part of the lens 1) and at the geometrical optical center, maintaining a distance between lenses ("DBL") space between the two pieces of surplus volume of optical material.

For the manufacturing of the ophthalmic lenses for twin rims and for the independent cutting of the requested right and left lens ophthalmic prescriptions, exactly equidistant with regard to the surface of the total horizontal length of the one-piece lens 1, this one-piece lens can be cut in two parts 3A and 3B.

For example, the piece 2 of optical material can have the following sizes: A=45 mm, B=35 mm; ED (effective diameter)=45 mm and DBL (Distance Between Lenses)=16 mm. The obtained ophthalmic lenses maintain their cleanliness and transparency for a longer period of time over their useful life, because they are integrated onto the one-piece lens 1.

The volume of the surplus optical material forming the optical piece 2 does not cover the whole internal surface of the one-piece lens 1.

The external surface of the one-piece lens 1 coincides with the abraded area of the volume of the internal optical material of the mask and both are integral parts jointly required for the requested ophthalmic prescriptions.

The one-piece lens 1 in the areas without the piece 2 of surplus volume of optical material has a minimum thickness of 1.8 mm, or thickness necessary to be considered safe for protection purposes, such as when used in impact protection masks, goggles or glasses.

Masks or the like with the one-piece lens 1 can receive all types of known protection and aesthetic coverings onto the front side, back side, or both sides.

The one-piece lens 1 and the piece 2 of surplus material volume preferably are made of the same optical material fused in one single piece and are constructed of any known type of optical material. In this way, in the case of photochromatic optical material with solar filter, transparent, polarized or of any optical embodiment, the whole device and its parts will be made of the same material, maintaining the optical and/or aesthetic qualities requested for specific prescription work.

The one-piece lens 1 of the wrap-around panoramic one-piece lens comprises side surpluses of material independently of the piece of optical material in order to allow the assembly on large frames, permitting one to offset the requested or needed optical geometry and the optical centers without affecting the successful adaptation of the prescription lenses of the wearer respecting segment heights and exact interpupillary distances.

The upper and lower temporal optical angles 5 of the one-piece lens 1 of the wrap-around panoramic one-piece lens comprise a rounded cut to prevent obstruction or disassembly through impact, during the cutting and polishing process in order to obtain the requested graduation.

For example, the one-piece lens 1 of semi-rectangular shape of the wrap-around panoramic one-piece lens has a horizontal length of 120 mm and a vertical width of 60 mm in order to permit successful assembly on large size solar and/or ophthalmic frames, without limiting the maximum sizes of the one-piece lens 1, while also meeting the needs in mask applications for several personal protection purposes. This engineering facilitates or permits weight balance, if the cutting and polishing process calls for rotation of the piece obtained under any conventional technique for cutting and generating conventional ophthalmic lenses.

The one-piece lens 1 of the wrap-around panoramic one-piece lens is made in standard sizes that adapt to all the shapes of the product for assembly purposes.

The one-piece lens 1 of a wrap-around panoramic one-piece lens can be contoured for obtaining the original design shapes or the shapes necessary for its assembly, using known cutting techniques, adapting their cutting lines to the frame design or to the chosen shape for precise assembly.

The one-piece lens 1 of a wrap-around panoramic one-piece lens can be cut by known technique, before or after cutting and generating the ophthalmic lenses obtained through known techniques, in order to obtain precise angular cuts impossible to reach with a conventional optical beveler.

The one-piece lens 1 of the wrap-around panoramic one-piece lens can be separated, through known cutting techniques, in two pieces, a right side piece and a left side piece, before or after cutting and generating the ophthalmic lenses obtained with known techniques, for assembly with the large and independent twin-rim frames, allowing, depending on the requirements, union at the center. This assembly system is applicable to most of the lenses of the solar, ophthalmic, sport and security industries.

The instant invention has been described and illustrated in its preferred embodiment; however, a person skilled in the art can contemplate variations that fall within the scope of the following claims.

The invention claimed is:

1. A wrap-around panoramic one-piece lens of optical material comprising an outside portion facing away from the wearer when in use and an inside portion facing the wearer when in use, wherein the inside portion has two surplus amounts of the same optical material as the lens, for the purpose of cutting ophthalmic lenses, said surplus amounts of material have a thickness and are positioned close to the central portion of the lens, so that the one-piece lens outside portion is smaller in thickness than the thickness of said surplus amounts throughout the areas where said surplus amounts of material are located, wherein the surplus amounts of material have the shape of a rounded edged irregular polygon and wherein the lens is semi-rectangular with rounded angles.

2. The one-piece lens according to claim 1, wherein each surplus amount of material has a vertical size of 45 mm and a horizontal size of 35 mm.

3. The one-piece lens according to claim 1, wherein the thickness of the lens in areas without surplus amounts of materials is a minimum of 1.8 mm.

4. The one-piece lens according to claim 1, wherein the external portion of the lens has a surface selected from the group consisting of toric base, bitoric base, spherical base, bispherical base, cylindrical base, bicylindrical base, aspherical base, biaspherical base, or combinations of them.

5. The one-piece lens according to claim 1 wherein the optical material is photochromatic or with solar filter or transparent or polarized material.

* * * * *